US006392089B1

(12) United States Patent
Falvey et al.

(10) Patent No.: US 6,392,089 B1
(45) Date of Patent: May 21, 2002

(54) PHOTORELEASABLE PROTECTING GROUPS ON ALCOHOLS, PHOSPHATES AND DIACIDS AND THE USE THEREOF

(75) Inventors: Daniel E. Falvey, Takoma Park; Kwangjoo Lee, Greenbelt, both of MD (US); Anamitro Banerjee, Ithaca, NY (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/541,063

(22) Filed: Mar. 31, 2000

Related U.S. Application Data
(60) Provisional application No. 60/127,230, filed on Mar. 31, 1999.

(51) Int. Cl.[7] ............................ C07C 61/00; C07C 69/76
(52) U.S. Cl. ........................ 562/400; 560/19; 560/103; 560/110; 560/111
(58) Field of Search ............................ 562/400; 560/19, 560/103, 110, 111

(56) References Cited

PUBLICATIONS

Banerjee et al., "Protecting groups that can be removed through photochemical electron transfer:Mechanistic and product studies on photosensitized release of carboxylates from phenacyl esters", J. Org. Chem. 62, pp. 6245–6251, 1997.*

Banerjeee et al., "Direct photolysis of phenacyl protecting groups studied by laser flash photolysis: An excited state hydrogen atom abstraction pathway leads to formation of carboxylic acids and acetpphenone", J. Am. Chem. Soc. 120, pp. 2965–2966, 1998.*

Corrie et al., "Synthetic, mechanistic and photochemical studies of phosphate esters of of substituted benzoins", J. Chem. Soc. Perkin Trans. I, pp. 2409–2417, 1992.*

Baldwin, J.E. et al., "New Photolabile Phosphate Protecting Groups," *Tetrahedron* 46:6879–6884, Pergamon Press (1990).

Banerjee, A. and Falvey, D., "Protecting Groups That Can Be Removed through Photochemical Electron Transfer: Mechanistic and Product Studies on Photosensitized Release of Carboxylates from Phenacyl Esters," *J. Org. Chem.* 62:6245–6251, American Chemical Society (1997).

Banerjee, A. et al., "Protecting Group Release Through Photoinduced Electron Transfer: Wavelength Control Through Sensitized Irradiation," *Tetrahedron Lett.* 39:4635–4638, Pergamon Press (Jun., 1998).

Banerjee, A. and Falvey, D.E., "Direct Photolysis of Phenacyl Protecting Groups Studied by Laser Flash Photolysis: An Excited State Hydrogen Atom Abstraction Pathway Leads to Formation of Carboxylic Acids and Acetophenone," *J. Am. Chem. Soc.* 120:2965–2966, American Chemical Society (Mar., 1998).

Banerjee, A. et al., "Photoreleasable Protecting Groups Based on Electron Transfer Chemistry. Donor Sensitized Release of Phenacyl Groups from Alcohols, Phosphates and Diacids," *Tetrahedron* 55:12699–12710, Pergamon Press (Oct., 1999).

Banerjee, A., *Photodeprotection of Carboxylic Acids and Alcohols Via Photoinduced Electron Transfer*, Doctoral Dissertation submitted to the University of Maryland, pp. 1–170 (Sep., 1999).

(List continued on next page.)

*Primary Examiner*—Ralph Gitomer
*Assistant Examiner*—Devesh Khare
(74) *Attorney, Agent, or Firm*—Sterne, Kessler, Goldstein, & Fox P.L.L.C.

(57) ABSTRACT

Alcohol, phosphate, and diacid derivatives that may be deprotected by irradiation are disclosed. The protecting group is an arylacyl or heteroarylacyl group.

6 Claims, 1 Drawing Sheet

OTHER PUBLICATIONS

Cameron, J.F. and Fréchet, J.M.J., "Photogeneration of Organic Bases from o–Nitrobenzyl–Derived Carbamates," *J. Am. Chem. Soc.* 113:4303–4313, American Chemical Society (1991).

Cameron, J.F. et al., "New Photolabile Amino Protecting Groups: Photogeneration of Amines from [(3'3, 5'–Dimethoxybenzoinyl)oxy]carbonyl Carbamates," *J. Chem. Soc., Chem. Commun. No.* 9:923–924, Chemical Society (1995).

Corrie, J.E.T. and Trentham, D.R., "Synthetic, Mechanistic and Photochemical Studies of Phosphate Esters of Substituted Benzoins," *J. Chem. Soc. Perkin Trans. I*, pp. 2409–2417, Chemical Society (1992).

Gee, K.R. et al., "Caged Bioactive Carboxylates. Synthesis, Photolysis Studies, and Biological Characterization of a New Caged N–Methyl–D–aspartic Acid," *J. Org. Chem.* 60:4260–4263, American Chemical Society (1995).

Gee, K.R. et al., "Desyl Esters of Amino Acid Neurotransmitters. Phototriggers for Biologically Active Neurotransmitters," *J. Org. Chem.* 61:1228–1223, American Chemical Society (1996).

Givens, R.S. et al., "Photochemistry of α–Keto Phosphate Esters: Photorelease of a Caged cAMP," *J. Am. Chem. Soc.* 114:8708–8710, American Chemical Society (1992).

Givens, R.S. and Keuper, W.L., III, "Photochemistry of Phosphate Esters," *Chem. Rev.* 93:55–66, American Chemical Society (1993).

Givens, R.S. et al., "Photochemistry of Phosphate Esters: α–Keto Phosphates as a Photoprotecting Group for Caged Phosphate," *J. Am. Chem. Soc.* 115:6001–6012, American Chemical Society (1993).

Givens, R.S. et al., "New Photoactivated Protecting Groups. 7. p–Hydroxyphenacyl: A Phototrigger for Excitatory Amino Acids and Peptides," *J. Am. Chem. Soc.* 119:8369–8370, American Chemical Society (1997).

McCray, J.A. et al., "A new approach to time–resolved studies of ATP–requiring biological systems: Laser flash photolysis of caged ATP," *Proc. Natl. Acad. Sci. USA* 77:7237–7241, The National Academy of Sciences of the USA (1980).

McGall, G. et al., "Light–directed synthesis of high–density oligonucelotide arrays using semiconductor photoresists," *Proc. Nat. Acad. Sci. USA* 93:13555–13560, The National Academy of Sciences of the USA (1996).

McGall, G.H. et al., "The Efficiency of Light–Directed Synthesis of DNA Arrays on Glass Substrates," *J. Am. Chem. Soc.* 119:5081–5090, American Chemical Society (1997).

Ottl, J. et al., "Preparation and Photoactivation of Caged Fluorophores and Caged Proteins Using a New Class of Heterobifunctional, Photocleavable Cross–Linking Reagents," *Bioconj. Chem.* 9:143–151, The American Chemical Society (Mar., 1998).

Peach, J.M. et al., "Photolabile Benzoin and Furoin Esters of a Biologically Active Peptide," *Tetrahedron* 51:10013–10024, Pergamon Press (1995).

Pirkle, W.H. and Simmons, K.A., "Improved Chiral Derivatizing Agents for the Chromatographic Resolution of Racemic Primary Amines," *J. Org. Chem.* 48:2520–2527, American Chemical Society (1983).

Pirrung, M.C. and Bradley, J–C., "Dimethoxybenzoin Carbonates: Photochemically–Removable Alcohol Protecting Groups Suitable of Phosphoramidite–Based DNA Synthesis," *J. Org. Chem.* 60:1116–1117, American Chemical Society (1995).

Pirrung, M.C. et al., "Inverse Phosphotriester DNA Synthesis Using Photochemically–Removable Dimethoxybenzoin Phosphate Protecting Groups," *J. Org. Chem.* 61:2129–2136, American Chemical Society (1996).

Pirrung, M.C., "Spatially Addressable Combinatorial Libraries," *Chem Rev.* 97:473–488, American Chemical Sociey (1997).

Pirrung, M.C. and Fallon, L., "Proofing of Photolithograhic DNA Synthesis with 3', 5'–Dimethoxybenzoinyloxycarbonyl–Protected Deoxynucleoside Phosphoramidites," *J. Org. Chem.* 63:241–246, American Chemical Society (Jan., 1998).

Prakash, G. and Falvey, D.E., "Model Studies of the (6–4) Photoproduct DNA Photolyase: Synthesis and Photosensitized Splitting of a Thymine—5,6–Oxetane," *J. Am. Chem. Soc.* 117:11375–11376, American Chemical Society (1995).

Rajasekharan Pillai, V.N., "Photoremovable Protecting Groups in Organic Synthesis," *Synthesis*, pp. 1–26, Georg Thieme Publishers (1980).

Sauers, C.K. et al., "The Alcohol–Bicarbonate–Water System. Structure–Reactivity Studies on the Equilibria for Formation of Alkyl Monocarbonates and on the Rates of Their Decomposition in Aqueous Alkali," *J. Am. Chem. Soc.* 97:5546–5553, American Chemical Society (1975).

Scannell, M.P. et al., "Model Studies of DNA Photorepair: Enthalpy of Cleavage of a Pyrimidine Dimer Measured by Photothermal Beam Deflection Calorimetry," *Photochem. Photobiol.* 64:764–768, American Society for Photobiology (1996).

Scannell, M.P. et al., "Model Studies of DNA Photorepair: Reduction Potentials of Thymine and Cytosine Cyclobutane Dimers Measured by Fluorescence Quenching," *J. Am. Chem. Soc.* 119:1971–1977, American Chemical Society (1997).

\* cited by examiner

PHOTORELEASABLE PROTECTING GROUPS ON ALCOHOLS, PHOSPHATES AND DIACIDS AND THE USE THEREOF

CROSS REFERENCE TO RELATED APPLICATION

The present application claims the benefit of U.S. provisional application No. 60/127,230 filed Mar. 31, 1999, the contents of which are fully incorporated by reference herein.

RELATED ART

Interest in photoreleasable protecting groups (PRPGs) has expanded in recent years as it has become clear that his technology can be applied to a variety of endeavors including, multi-step organic synthesis (Greene, T. W. and Wuts, P. G. M., *Protective Groups in Organic Synthesis*, Wiley, New York, N.Y. (1991), p. 473; Pillai, V. N. R., *Synthesis:* 1–26 (1980)), time resolved x-ray crystallography (Schlichiting et al., *Nature* 345:309–315 (1990)), photolithographic fabrication of DNA chips (Lockhart et al., *Nature Biotechnol.* 14:1675–1680 (1996); Pirrung, M. C., *Chem. Rev.* 97:473–488 (1997); Fodor et al.,*Science* (Washington, D.C.) 251:767–773 (1991); Pirrung et al., *J. Org. Chem.* 63:241–246 (1998)), photoregulation of proteins and cellular signaling pathways (Curley, K. and Lawrence, D.S.,*J. Am. Chem. Soc.* 120:8573–8574 (1998); Wood et al., *J. Am. Chem. Soc.* 120:7145–7146 (1998); Pollit, S. K. and Schultz, P. G.,*Angew. Chem. Int. Ed. Engl.* 37:2104–2107 (1998); Porter, et al., in *Biological Applications of Photochemical Switches*, H. Morrison, ed.; Wiley, New York, N.Y. (1993), pp. 197–242) and studies of ion channel dynamics in whole cells (Hess, G. P. and Grewer, C., *Methods in Enzymology* 291:443–473 (1998); Gee et al., *J. Org. Chem.* 61:1228–1233 (1996); Rossi et al., *J. Biol. Chem.* 272:32933–32939 (1997)). There are a number of established strategies for masking and photolytically releasing various functionalities. PRPGs based on derivatives of the ortho-nitrobenzyl group are perhaps the most widely used (Ottl et al., *Bioconjugate Chem.* 9:143–151 (1998); McCray et al., *Proc. Natl. Acad, Sci. USA* 77:7273–7241 (1980); Gee et al., *J. Org. Chem.* 60:4260–4263 (1995); Cameron, J. F. and Frechet, J. J. M., *J. Am. Chem. Soc.* 113:4303–4313 (1991)). More recent investigations have identified the α-benzoin group and its derivatives as an alternative strategy (Peach et al., *Tetrahedron* 51:10013–10024 (1995); Pirrung et al., *J. Org Chem.* 63:241–246 (1998); Pirrung, M. C. and Bradley, J.,*J. Org. Chem.* 60:1116–1117 (1995); Sheehan, J. C. and Wilson, R. M.,*J. Am. Chem. Soc.* 86:5277–5281 (1964); Rock, R S. and Chan, S. I., *J. Am. Chem. Soc.* 120:10766–10767 (1998); Cameron et al., *J. Chem. Soc. Chem. Commun.* 923–924 (1995)). The latter releases the target functionality more rapidly following absorption of the photon and gives by-products that are generally more inert than those from the ortho-nitrobenzyl family. Lately, Givens, et al. (Givens et al., *J. Am. Chem. Soc.* 119:8369–8370(1997); Gee et al.,*J. Org. Chem.* 61:1228–1233 (1996))have demonstrated the utility of the 4-hydroxyphenacyl group. One problem that remains in this area is control of the wavelengths required for functional group release. Most of the currently available technologies utilize wavelengths in the UV-B region of the spectrum, limiting their applicability in situations where the target molecule or other species in the matrix absorb in the same spectral region.

In a series of recent papers (Banerjee et al., *Tetrahedron Lett.* 39:4635–4638 (1998); Banejee, A. and Falvey, D. E., *J. Am. Chem. Soc.* 120:2965–2966 (1998); Banerjee, A. and Falvey, D. E., *J. Org Chem.* 62:6245–6251 (1997)), a modular approach to the design of PRPGs was advanced whereby the light absorption step is controlled by one element (an antenna or a sensitizer) and the bond scission step leading to release of the target molecule is controlled by a separate element (release group). In principle, such a strategy permits separate optimization of the wavelengths of light required for release and the rates and efficiencies of the bond scission process. This concept has been experimentally realized through the release of carboxylic acids from phenacyl esters 1a (infra) (Banerjee, A. and Falvey, D. E., *J. Org. Chem.* 62:6245–6251 (1997)). In this case the phenacyl group acts as the release group and the light absorption step is controlled by a separate molecule which functions as an electron donating sensitizer. The initial photochemical step is transfer of an electron from the excited sensitizer to the phenacyl group, generating a phenacyl anion radical 2. The latter rapidly eliminates a carboxylate anion. It was demonstrated that a variety of carboxylic acids could be released using this strategy.

SUMMARY OF THE INVENTION

The invention relates to the electron transfer mediated photochemical release of alcohols, phosphates and diacids. The alcohols are protected as mixed heteroarylacyl and arylacyl carbonate esters. Irradiation of mixtures containing electron donating sensitizers and the carbonate esters initiates a series of bond scission reactions that result in clean release of the corresponding alcohols. This was demonstrated for a variety of protected primary, secondary and tertiary hydroxyl groups, including the 5'-hydroxy group of thymidine. Examples of sensitizers that are effective in promoting photolytic release include 9,10-dimethylanthracene and 9-methylcarbazole. GC/MS and NMR analysis of the by-products formed in these release reactions implicates the intermediacy of radical ion intermediates in these reactions. It is further demonstrated that the electron transfer sensitized release method can be extended to phosphate esters and di-functional acids.

In particular, the invention relates to a compound having the Formula:

wherein
 $R^1$ is an aryl or heteroaryl group; and
 X is one of $OCO_2R^2$ or $OP(O)(OR^3)_2$, wherein $R^2$ and $R^3$, each independently, are the residue of an alcohol containing compound (i.e. $R^2$ or $R^3$, together with the neighboring oxygen, when bound to hydrogen, is the alcohol).

The invention also relates to a compound having the Formula:

wherein
 $R^1$ is an aryl or heteroaryl group, n is 2–6, and

Z is the residue of any compound having two or more carboxyl groups.

The invention also relates to a method of preparing a protected compound having the Formula:

wherein

R¹ is an aryl or heteroaryl group; and

X is $OCO_2R^2$, wherein $R^2$ is the residue of an alcohol containing compound, comprising condensing the chloroformate derivative of the alcohol with the compound having Formula:

under conditions whereby said protected compound is produced.

The invention also relates to a method of preparing a protected compound having the Formula:

wherein

R¹ is an aryl or heteroaryl group; and

X is $OCO_2R^2$, wherein $R^2$ is the residue of an alcohol containing compound, comprising reacting the alcohol with N,N-carbonyldiimidazole or phosgene, and then adding the compound having Formula:

under conditions whereby said protected compound is produced.

The invention also relates to a method of preparing a protected compound having the Formula:

wherein

R¹ is an aryl or heteroaryl group; and

X is $OCO_2R^2$, wherein $R^2$ is the residue of an alcohol containing compound, comprising reacting methyl triflate together with N,N-carbonyldiimidazole, then adding the alcohol, and then adding the compound having Formula:

under conditions whereby said protected compound is produced.

The invention also relates to a method of preparing a protected compound having the Formula:

wherein

R¹ is an aryl or heteroaryl group; and

X is $OP(O)(OR^3)_2$, wherein $R^3$ is the residue of an alcohol containing compound, comprising reacting the compound having Formula:

with a compound having the Formula:

under conditions whereby said protected compound is produced.

The invention also relates to a method of preparing a protected compound having Formula:

wherein

R¹ is an aryl or heteroaryl group, n is 2–6, and

Z is the residue of a compound having two or more carboxyl groups; comprising reacting the compound having Formula:

with a compound having Formula:

under conditions whereby said protected compound is produced.

The invention also relates to a method of deprotecting a compound having the Formula:

wherein
R¹ is an aryl or heteroaryl group; and
X is OCO₂R², wherein R² is the residue of an alcohol containing compound, comprising irradiating said compound in the presence of a sensitizer under conditions whereby said compound is deprotected and the alcohol containing compound is produced.

The invention also relates to a method of deprotecting a compound having the Formula:

wherein
R¹ is an aryl or heteroaryl group; and
X is OP(O)(OR³)₂, wherein R³ is the residue of an alcohol containing compound, comprising irradiating said compound in the presence of a sensitizer under conditions whereby said compound is deprotected and the alcohol containing compound is produced.

The invention also relates to a method of deprotecting a compound having Formula:

wherein
R¹ is an aryl or heteroaryl group,
n is 2–6, and
Z is the residue of a compound having two or more carboxyl groups; comprising irradiating said compound in the presence of a sensitizer under conditions whereby said compound is deprotected and the alcohol containing compound is produced.

DESCRIPTION OF THE PREFERRED EMBODIMENTS

The present invention relates to the photolytic release of protected alcohols, phosphates and diacids. In each case, electron transfer from an excited state aromatic compound (a "sensitizer") to an aryl or heteroaryl acyl group is used as the method of photorelease. Extension of this procedure to alcohols requires that the hydroxyl group be masked as a mixed carbonate ester (e.g., 1d). Phosphates, on the other hand can be protected as aryl and heteroaryl acyl esters. It is further demonstrated that this method can be applied to functionally complex systems. Diacids can be doubly masked with aryl and heteroaryl acyl groups and sequentially released.

Analysis of reaction mixtures by GC/MS and ¹H NMR spectroscopy shows that the sensitizer is consumed in subsequent radical reactions of the fragments.

Scheme 1 a: X=OCOR; b: X=OR; c: X=OPh; d: X=OCO₂R; e: X=OP(O)(OR)₂

Thus, the invention relates to protected alcohols having the Formula:

wherein
R¹ is an aryl or heteroaryl group; and
X is one of OCO₂R² or OP(O)(OR³)₂, wherein R² and R³, each individually, are the residue of an alcohol containing compound. R² and R³ include without limitation alkyl, alkenyl, alkynyl, aryl, aralkyl, aralkenyl, aralkynyl, fused aryl, carbocyclic, carboxylalkyl-substituted alkyl, heterocycloalkyl, heterocycloalkyl-substituted alkyl, heteroaryl, heteroarylalkyl, heteroarylalkenyl, and heteroaralkynyl groups, any one of which may be optionally substituted with one or more alkyl, alkenyl, alkynyl, alkoxy, acyl (alkanoyl), acyloxy, cyano, alkylcarboxy, chloro, bromo, aryl, cycloalkyl, aralkyl, aralkenyl, aralkynyl, hydroxy, nitro, amino or carboxy groups. Other alcohol containing compounds include sugars and sugar derivatives such as the RNA and DNA bases as well as peptides and proteins containing tyrosine.

In particular, the invention relates to the protected alcohols have the following Formulae:

wherein $R^1$–$R^3$ are as defined above.

The invention also relates to protected polyfunctional carboxylic acids having the Formula:

wherein $R^1$ is as defined above, n is 2–6, and Z is the residue of any compound having two or more carboxyl groups. Examples of Z include without limitation alkylene and phenylene, either of which may be optionally substituted with one or more alkyl, alkenyl, alkynyl, alkoxy, acyl (alkanoyl), alkylcarboxy, fluoro, chloro, bromo, aryl, heteroaryl, cycloalkyl, aralkyl, aralkenyl, aralkynyl, hydroxy, nitro, amino or carboxy groups; and amino acids, peptides and proteins having multiple carboxy groups.

Preferred compounds have the Formula:

Particular examples of compounds having two or more carboxyl groups include malonic acid, succinic acid, and o-, m-, and p-phthalic acid. Other compounds having two or more carboxy groups include aspartic acid, glutamic acid (e.g in the N-protected forms such as the t-BOC, N-acetyl and benzyloxycarbonyl derivatives), peptides and proteins comprising aspartate or glutamic acid at the N-terminus, as well as peptides and proteins having two or more aspartic acid and/or glutamic acid residues. See those peptide sequences described in WO99/18856.

Useful alkyl groups include straight-chained and branched $C_{1-10}$ alkyl groups, more preferably $C_{1-16}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkylene groups include $C_{1-10}$ alkylene groups, more preferably $C_{1-6}$ alkylene groups. Typical $C_{1-10}$ alkylene groups include methylene, ethylene, propylene, butylene, pentylene, hexylene and octylene groups, which can be optionally substituted.

Useful alkenyl groups include straight-chained and branched $C_{2-10}$ alkenyl groups, more preferably $C_{2-6}$ alkenyl groups. Typical $C_{2-10}$ alkenyl groups include ethenyl, propenyl, isopropenyl, butenyl, sec-butenyl, 3-pentenyl, hexenyl and octenyl groups, which can be optionally substituted.

Useful alkynyl groups include straight-chained and branched $C_{2-10}$ alkynyl groups, more preferably $C_{2-6}$ alkynyl groups. Typical $C_{2-10}$ alkynyl groups include ethynyl, propynyl, butynyl, pentynyl, hexynyl and octynyl groups, which can be optionally substituted.

Useful alkoxy groups include oxygen substituted by one of the $C_{1-10}$ alkyl groups mentioned above, which can be optionally substituted.

Useful amino groups include —$NH_2$, —$NHR_4$ and —$NR_5R_6$, wherein $R_4$, $R_5$ and $R_6$ are $C_{1-10}$ alkyl or cycloalkyl groups, or $R_5$ and $R_6$ are combined with the N to form a ring structure, such as a piperidine, or $R_5$ and $R_6$ are combined with the N and other group to form a ring, such as a piperazine. The alkyl groups can be optionally substituted.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful arylalkyl groups include any of the above-mentioned $C_{1-10}$ alkyl groups substituted by any of the above-mentioned $C_{6-14}$ aryl groups. Preferably the arylakyl group is benzyl, phenethyl or naphthylmethyl.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl.

Sugars which can be protected according to the invention include without limitation glucose, mannose, galactose, gulose, allose, altrose, idose, talose, fructose, arabinose, xylose, sucrose, cellobiose, maltose, lactose, trehalose, gentiobiose, melibiose, raffinose, and gentianose. In apreferred embodiment, the primary hydroxy group is selectively protected with about one equivalent of the aryl or heteroaryl acyl alcohol. Alternatively, substantially all of the hydroxy groups may be protected by treating with a large excess of aryl or heteroaryl acyl alcohol and other condensing reagents.

Examples of RNA and DNA bases that may be protected at the 5'-position according to the present invention include adenosine, deoxyadenosine, guanosine, deoxyguanosine, cytidine, deoxycytidine, uridine and deoxythymidine. The phosphate groups of the corresponding mono-, di- and triphosphates (e.g. at the 3'- or 5'-position) and cyclic phosphates (e.g. cyclic AMP) may also be protected according to the present invention using methods analogous to those employed in the solid phase synthesis of oligonucleotides, e.g. with the corresponding cyanoethyl phosphoramidates of the protected bases (where necessary). See See Eckstein, F., Oligonucleotides and Analogs A Practical Approach, IRL Press, New York, N.Y. (1991).

The invention relates to a method of deprotecting a compound having the Formula:

wherein $R^1$ is an aryl or heteroaryl group; and

X is $OCO_2R^2$, wherein $R^2$ is the residue of an alcohol containing compound, comprising irradiating said compound in the presence of a sensitizer under conditions whereby said compound is deprotected and the alcohol containing compound is produced.

The invention also relates to a method of deprotecting a compound having the Formula:

wherein $R^1$ is an aryl or heteroaryl group; and

X is $OP(O)(OR^3)_2$, wherein $R^3$ is the residue of an alcohol containing compound, comprising irradiating said compound in the presence of a sensitizer under conditions whereby said compound is deprotected and the alcohol containing compound is produced.

The invention also relates to a method of deprotecting a compound having Formula:

wherein $R^1$ is an aryl or heteroaryl group, n is 2–6, and

Z is the residue of a compound having two or more carboxyl groups; comprising irradiating said compound in the presence of a sensitizer under conditions whereby said compound is deprotected and the alcohol containing compound is produced.

A variety of sensitizers can be used in these deprotection reactions. Such sensitizers include any compound capable of donating an electron in its excited state, more specifically, when the excited state oxidation potential is less than about −1.9 V. Such sensitizers include without limitation benzene substituted by one or more electron donating groups, optionally substituted fused polycyclic aromatics, and optionally substituted polycyclic heteroaromatics. The electron donating groups that may be substituted on benzene include without limitation amino, monoalkyl amino, dialkylamino, hydroxy, alkoxy, and aryloxy. Examples offused polycyclic aromatics include without limitation naphthalene, anthracene, phenanthrene, acenaphthalene, fluoranthrene, and pyrene. Substituents that may be present on the polycylic aromatics include one or more amino, monoalkyl amino, dialkylamino, alkoxy, aryloxy, alkylthio, hydroxy, alkyl, bromo, chloro, nitro, acylamino, and carboxy.

Examples of polycyclic heteroaromatics that can be use include those containing $sp^3$ hybridized heteroatoms, e.g. thiophene, furan, pyrrole, naphtho[2,3-b]thiophene, carbazole, and perimidine. Substituents that may be present on the polycyclic heteroaromatics include one or more amino, monoalkyl amino, dialkylamino, alkoxy, aryloxy, alkylthio, hydroxy, alkyl, bromo, chloro, nitro, acylamino, and carboxy.

Especially preferred sensitizers include 9-methylanthracene, 9,10-dimethylanthracene, 2-aminoanthracene, 2-naphtholate and 2-phenanthrolate which absorb light at relatively high wavelengths. Most preferred sensitizers have a $\lambda_{max}$ in the range of about 340–450 nm, more preferably, 380–410 nm.

In the case of hydroxy substituted sensitizers, the reaction may be carried out in the presence of a base that abstracts the proton on the hydroxy group of the sensitizer. Examples of such bases include sodium, potassium and calcium carbonate, sodium and potassium hydroxide, alkylamines, dialkylamines and trialkylamines, and dimethylaminopyridine.

As discussed in more detail below, preferred sensitizers allow for photolysis at high wavelengths (>390 nm). Such sensitizers avoid problems associated with competing absorption by the substrates and, thus, widen the applicability of the technology. Further, high wavelength light sources are generally more readily available, less expensive, safer to operate and do not require special glassware.

The deprotection reaction may be carried out in any polar solvent including without limitation water, methanol, ethanol, ethylene glycol, DMF, DMSO, and the like. The solution containing the protected compound is generally purged with an inert gas (e.g. $N_2$ or Ar) prior to the deprotection reaction.

The temperature of the reaction solution is generally above the freezing point of the solvent and below the boiling point. Preferably, the reaction is carried out at about 20–35° C., most preferably, at about room temperature.

The ratio of sensitizer to substrate in the reaction solution is generally above one since the sensitizer is consumed in the reaction. Preferably, the ratio is about 1.5:1 to about 2:1, although a larger excess of the sensitizer may be employed.

In a preferred embodiment, less than one equivalent of the sensitizer is employed and a sacrificial electron donor is added to the reaction mixture. In this embodiment, the sensitizer is recycled. The sensitizer may be present at 10 mole percent or greater compared to the substrate and an excess (up to 200 mole percent or greater) of the sacrificial donor may be employed. Examples of such sacrificial electron donors include without limitation EDTA, ascorbic acid, and N-phenylglycine.

The concentration of the substrate may range from about 10 μM to about 100 mM, preferably at least about 500 μM. At lower concentrations, the reaction proceeds more slowly. In general, the reaction takes about 1 min to 2 days depending on the concentrations of the reactants and the strength of the irradiation lamp. The course of the reaction may be monitored by NMR, HPLC, GC and/or GC/MS.

In carrying out the reaction, it is preferred that a high pass glass filter to avoid competing absorption by the substrates. Such high pass filters are readily available from Corning Glass, Edmund Scientific, Oriel Instruments and Melles Griot. The choice of filter depends on the $\lambda_{max}$ of the senisitzer. In general, one may choose a filter having a cut offjust below the $\lambda_{max}$ of the senisitzer, e.g. for 2-aminoanthracene having a $\lambda_{max}$ of 402, a 395 nm cut off filter may be employed. For carbazole having a $\lambda_{max}$ of 345, a 320 nm cut off filter may be employed. Those of ordinary skill in the art can choose other filters suitable for other sensitizers with no more than routine experimentation.

Lamps which may be used include a 350 W Xe lamp available from Oriel Instruments and the Ace-Hanovia 450

W medium pressure Hg vapor lamp. It is most preferred that the irradiation comprises wavelengths in the range about 340–50 nm and that a sensitizer is employed with a $\lambda_{max}$ in this range.

The reaction may be carried out in any standard transparent borosilicate laboratory glasswear including PYREX glass as well as quartz glass.

It was clear at the outset of this study that adapting the phenacyl methodology to release of alcohols by simply photolyzing phenacyl ethers (1b) was unlikely to be successful. Wayner, et al. (Andersen et al., *J. Am. Chem. Soc.* 118:4871–4879 (1996)) have shown that rates of bond scission in anion radicals correlates with the basicity of the anionic fragment, the more basic anions being eliminated much more slowly than less basic anions. It follows then that the more basic alkoxide anion would be eliminated more slowly from a phenacyl ether than the less basic carboxylate from a phenacyl ester. In a practical sense, these slower rates would manifest themselves in a reduction of quantum yields of the release step to the point where unacceptably long exposure times would be required to achieve release of the substrate.

Preliminary, sensitized deprotection experiments on α-phenoxyacetophenone 1c were carried out. The phenoxide leaving group is less basic than typical alkoxides but more basic than the carboxylates. Therefore, it was anticipated that this would represent a best case situation for the phenacyl ethers. In fact laser flash photolysis studies by the Wayner group show that this anion radical does eliminate phenoxide with rate constants $<10^6$ s$^{-1}$ (Mathivanan, N. et al., *J. Phys. Chem.* 99:8190–8195 (1995)). Nonetheless exhaustive photolysis of mixtures of the sensitizers and 1c failed to produce any detectable amounts of phenol. Apparently the release of phenoxide is insufficiently rapid to compete with back electron transfer in the geminate solvent cage.

Unsymmetric phenacyl carbonates (1d) were next examined. The mechanism in Scheme 1 predicts that the key bond scission step is release of a monoalkyl carbonate anion 3. These species possess basicities closer to the carboxylates than to the alkoxides and thus the bond scission rate should be rapid enough to allow for good conversions in reasonable exposure times. Monoalkylcarbonates are well known to expel $CO_2$ ultimately forming the corresponding alcohols (Scheme 2) (Sauers et al, *J. Am. Chem. Soc.* 97:5546–5553 (1975)). A similar strategy has been used to extend the capabilities of other PRPG's (Cameron, J. F. and Frechet, J. J. M., *J. Am. Chem. Soc.* 113:4303–4313 (1991); Pirrung, M. C. and Bradley, J., *J. Org. Chem.* 60:1116–1117 (1995); Cameron J. et al., *Chem. Soc. Chem. Commun.* 923–924 (1995)).

Scheme 2

The invention relates to a method of preparing a protected compound having the Formula:

wherein
  $R^1$ is an aryl or heteroaryl group; and
  X is $OCO_2R^2$, wherein $R^2$ is the residue of an alcohol containing compound, comprising condensing the chloroformate derivative of the alcohol with the compound having Formula:

under conditions whereby said protected compound is produced. In general, such conditions include the presence of a base such as pyridine and, optionally, a polar, aprotic solvent.

The invention also relates to a method of preparing a protected compound having the Formula:

wherein
  $R^1$ is an aryl or heteroaryl group; and
  X is $OCO_2R^2$, wherein $R^2$ is the residue of an alcohol containing compound, comprising reacting the alcohol with N,N-carbonyldiimidazole or phosgene, and then adding the compound having Formula:

under conditions whereby said protected compound is produced. In general, such conditions include carrying out the reaction in a polar, aprotic solvent.

The invention also relates to a method of preparing a protected compound having the Formula:

wherein
  $R^1$ is an aryl or heteroaryl group; and
  X is $OCO_2R^2$, wherein $R^2$ is the residue of an alcohol containing compound, comprising reacting methyl triflate together with N,N-carbonyldiimidazole, then adding the alcohol, and then adding the compound having Formula:

under conditions whereby said protected compound is produced. In general, such conditions include carrying out the reaction in a polar, aprotic solvent.

The invention also relates to a method of preparing a protected compound having Formula:

wherein
  $R^1$ is an aryl or heteroaryl group,
  n is 2–6, and

Z is the residue of a compound having two or more carboxyl groups; comprising reacting the compound having Formula:

with a compound having Formula:

under conditions whereby said protected compound is produced.

The synthesis of phenacylalkyl carbonates is exemplified in Scheme 3. Where the corresponding chloroformate 4 (for methanol, ethanol, and benzyl alcohol) is available, it is most convenient to couple the latter with phenacyl alcohol. Higher yields could be achieved when the coupling was carried out by first activating the alcohol with N,N-carbonyldiimidazole 5 and then adding phenacyl alcohol. Thymidine and isopropyl alcohol were protected by the methylimidazolium complex of phenacyl alcohol 6 (Pirrung, M. C. and Bradley, J., *J. Org. Chem.* 60:1116–1117(1995)). The latter was generated from phenacyl alcohol, 5, and methyltriflate. The yields of the protection step were highly dependent on the presence of traces of water in the solvent. The protection yields in Table 1, which represent typical rather than optimal conditions, ranged from 88 to 38%. The lowest yields were for tert-butyl alcohol and thymidine. These are attributed to steric hindrance in the first case and the low solubility of the substrate in the second case.

Scheme 3

Photolytic release of each alcohol was achieved through irradiation of $N_2$-purged $CH_3CN$ solutions containing the phenacylalkyl carbonate (40–60 $\mu$mol) along with an appropriate electron donor sensitizer (typically 60–90 $\mu$mol). For most trials, the mixtures were irradiated in sealed NMR tubes and the consumption of the substrate and the appearance of the product could be monitored at various periods through out the photolysis.

Clean conversion of the carbonate to the alcohol was observed in each 15 case. The yield of alcohol could be calculated by comparison of its $^1$H NMR peak integration to that of an internal standard. Modest to excellent yields of the released alcohols are observed. This photorelease strategy does not appear to be strongly dependent on the type of alcohol. Methyl, primary, secondary and tertiary alcohols were released in reasonable yields. Aryl-substituted alcohols, benzyl and phenethyl alcohols were also released efficiently.

Chart 1: Excited State Electron Donors

TABLE 1

Photorelease of Alcohols from Sensitized Photolysis of Phenacyl
Alkyl Carbonates (ROCO$_2$CH$_2$COPh) in CH$_3$CN

| RO— | Sensitizer[a] | Conditions | Protection Yield | Yield of ROH (%) |
|---|---|---|---|---|
| CH$_3$O— | 9,10-dMA | 3 h, >390 nm | 64 | 83 |
| CH$_3$CH$_2$O— | 9,10-dMA | 1 h, >390 nm | 60 | 66 |
| (CH$_3$)$_2$CHO— | 9-MC | 1.5 h, >320 nm | 88 | 65 |
|  | TMPD | 1.5 h, >320 nm |  | 84 |
| (CH$_3$)$_3$CO— | 9,10-dMA | 2 h, >390 nm | 38 | 61 |
| PhCH$_2$O— | TMPD | 2 h, >320 nm | 88 | 72 |
| PhCH$_2$CH$_2$O— | 9,10-dMA | 3 h, >390 nm | 74 | 81 |
|  | 9-MC | 4 h, >320 nm | 48 | 81 |
|  | 9,10-dMA | 4 h, >390 nm |  | 91 |

[a]Sensitizers: 9,10-dMA = 9,10-dimethylanthracene; 9-MC = 9-methylcarbazole; TMPD = N,N,N',N'-tetramethyl-p-phenylenediamine.

Studies were carried out using the three sensitizers indicated in Chart 1. These are all excited state electron donors which have previously been shown to be effective at reducing the phenacyl group. 9,10-Dimethylanthracene (9,10-dMA) has an excited state oxidation potential of −2.23 V (vs. SCE) and its highest wavelength absorption maximum is at 398 nm. 9-Methylcarbazole (9-MC) is a slightly better donor, having an excited state oxidation potential of −2.46 V but absorbs at lower wavelengths (λ=345 nm). Finally N,N,N',N'-tetramethyl-para-phenylenediamine (TMPD) has $E_{ox}^* = -3.25$ and $\lambda_{max} = 332$ nm.

One well-established application ofphotolytic release of alcohols is in the fabrication of solid state combinatorial libraries of oligonucleotides, or "DNA-chips" (Pirrung et al., *J. Org. Chem.* 63:241–246 (1998); McGall et al., *J. Am. Chem. Soc.* 119:5081–5090 (1997); McGall et al., *Proc. Natl. Acad. Sci. USA* 93:13555–13560 (1996)). In this embodiment, the 3'-group of the nucleoside is linked to a solid phase (e.g. with a succinyl group attached to a bead of borosilicate glass) according to well known methods. See Eckstein, F., Oligonucleotides and Analogs A Practical Approach, IRL Press, New York, N.Y. (1991). For this reason, the 5'-(phenacylcarbonate) ester of thymidine was protected and its sensitized photorelease was examined. In this case the unprotected alcohol, thymidine was insufficiently soluble in CD$_3$CN for observation by $^1$H NMR. However the product could be conveniently isolated by simply filtering the reaction mixture. In this case the yield was determined by weighing the solid. Its purity was confirmed by $^1$H NMR in DMSO-d$_6$.

The invention also relates to a method of preparing a protected compound having the Formula:

wherein
R$^1$ is an aryl or heteroaryl group; and

X is OP(O)(OR$^3$)$_2$, wherein R$^3$ is the residue of an alcohol containing compound, comprising reacting the compound having Formula:

with a compound having the Formula:

under conditions whereby said protected compound is produced. In general, such conditions include the presence of a base such as pyridine and, optionally, a polar aprotic solvent.

The phosphate group is ubiquitous in biochemistry and many strategies for triggering or otherwise controlling biological systems rely on methods for the photochemical release of this finctional group (Baldwin et al., *Tetrahedron* 46:6879–6884 (1990); Corrie, J. E. T. and Trentham, D. R., *J. Chem. Soc. Perkin Trans I:*2409–2417 (1992); Pirrung et al., *J. Org. Chem.* 61:2129–2136 (1996); Givens, R. S. and Kueper, L. W., *Chem. Rev.* 93:55–66 (1993)). The phenacyl ester of diethylphosphphate 1e was synthesized by combining diethylphosphoryl chloride with phenacyl alcohol in the presence of a base such as pyridine (Scheme 4). Irradiation of a mixture of protected phosphate 1e and 9,10-dMA were carried out using the same conditions employed for the carbonates. As with the carbonates, the consumption of the ester and the growth of the diethyl phosphoric acid could be monitored as the sample was photolyzed in a sealed $^1$H NMR tube. Thus the OCH$_2$ resonance at 4.15 ppm was observed to disappear with photolysis and concomitant with the appearance of the same group in diethyl phosphoric acid at 4.01 ppm. The conversion was quantitative and no side products could be detected, other than some aromatic reso- nances which can be attributed to sensitizer by-products (vide infra). Similar results were obtained when 1e is photolyzed with N,N-dimethylaniline, using a 290 nm cutoff filter.

Scheme 4

There are many interesting biological molecules which possess several different sites with the same functional group. For example carbohydrates contain several hydroxyl groups, and large proteins will usually possess multiple copies of amino acids with functional side-chains (e.g. serine, glutamate, aspatate, etc). Phototriggered release of such complex molecules will require that sequential elimination of the two protecting groups occur cleanly and that the released finctional group or accumulated by-products do not interfere with subsequent deprotection steps. For this reason it was interesting to determine if it would be possible to release two phenacyl groups from different sites on the same molecule.

To this end two diacids, malonic acid and N-t-Boc-glutamic acid were each protected with two equivalents of phenacyl bromide. These protection reactions proceeded cleanly and gave good yields of the diesters 7 and 8, respectively. Sensitized photolysis (using 9,10-dMA and the same conditions employed for the carbonates) of both 7 and 8 cleanly released the corresponding acids (Scheme 5). In the case of malonic acid the overall deprotection yield was 83% and in the case ofN-t-Boc-glutamic acid the yield was 87%. Monitoring the malonic acid reaction by $^1$H NMR showed the accumulation of mono-phenacylmalonate at intermediate times. For example after 15 min of photolysis there was detected the intermediate monoester (34%, observed by its characteristic $CH_2$ group $^1$H NMR resonance at 3.55 prn), unconverted diester (59%, 3.75 ppm), and malonic acid (5% 3.34 ppm). After 2 h of photolysis only the deprotected diacid was seen. In the case of 6, $^1$H NMR analysis of the photolysate at intermediate times during the photolysis also showed additional peaks apparently associated with the two possible monoesters. However the high complexity of the $^1$H NMR spectrum precluded certain assignment and quantitation of the intermediate peaks. After 2 h of photolysis only the deprotected substrate was seen (along with sensitizer and its byproducts).

Scheme 5

The mechanism in Scheme 1 predicts that aphenacyl radical ($PhCOCH_2$·) and the cation radical of the sensitizer remain after release of the functional group. The fates of these species were discussed in previous papers for the case where the sensitizer is an alkyl aniline derivative (e.g. N,N-dimethylaniline) (Banerjee, A. and Falvey, D., *J. Org. Chem.* 62:6245–6251 (1997)). Briefly, the arylamine cation radical is deprotonated on the carbon immediately adjacent to the N-atom. This provides a strongly reducing a-amino radical which apparently donates an electron to the phenacyl radical giving acetophenone enolate and an iminium ion. Hydrolysis of the latter and protonation of the former gives the observed products, the de-alkylated aniline derivative along with acetophenone. The sensitizers TMPD and 9-MC are alkylarylamines and therefore it was assumed that they follow the previously characterized mechanism. The 9,10-dMA sensitizer, on the other hand, is not an alkylaryl amine, and thus the fates of the radicals from this sensitizer also need to be considered.

The by-products detected from the 9,10-dMA sensitized photolyses indicate that analogous free radical and radical ion intermediates are formed. 9,10-Dimethylanthracene was photolyzed in presence of phenacyl 5'-thymidine carbonate. After the photolysis, the solvent was evaporated under reduced pressure. The resulting white residue was washed twice with $CHCl_3$. $^1H$ NMR analysis of the soluble fraction revealed a mixture of several aromatic compounds, including dMA-dimer 9. The latter was identified through its characteristic resonances at 4.0 and 3.1 ppm (Becker et al., *J. Org. Chem.* 44:4247–4251 (1979)). GC/MS analysis of the same mixture showed peaks with masses characteristic of acetophenone (m/z=120), 1,2-dibenzoylethane 10 (m/z=238), and dMA-phenacyl coupling product, 11 (m/z=324). The same photolysis was carried out with a large excess of 1,4-cyclonexadiene, a good H atom donor. The effect of this trap was to increase the yield of acetophenone and 9,10-dimethylanthmene at the expense of the radical coupling products.

The above results support the mechanism for 9,10-dMA sensitized deprotection shown in Scheme 6. Electron transfer from the excited singlet state of 9,10-dMA to the phenacyl carbonate provides a radical ion pair. The phenacyl carbonate radical anion (2) undergoes a heterolytic C—O scission to give the phenacyl radical ($PhCOCH_2$.) and the cation radical of 9,10-dMA (12). The latter is known to be a rather strong acid ($pK_a$=−5.0) (Zhang et al., *J. Org. Chem.* 58:3051–3059 (1993)) and would be rapidly deprotonated (either by the monoalkyl carbonate, the alkoxide or the solvent) giving dMA radical (13). The observed by-products result from coupling and cross-coupling of radicals $PhCOCH_2$. and 13.

Scheme 6

The present invention may utilize a wide variety of photosensitizers allowing for wavelengths approaching the visible. Phenacyl phenylacetate was chosen as a model protected acid that releases phenylacetic acid upon sensitized irradiation.

The protection of the acid was carried out by well described procedures 10 (Banerjee, A. and Falvey, D. E., *J. Org. Chem.* 62:6245–6251 (1997)). About 0.8 equivalents of phenacyl bromide was added to a solution of DBU and the acid in benzene. The resulting mixture was stirred for about 2 h at room temperature. The resulting solution was washed with 10% HCl, and $NaHCO_3$, dried over $MgSO_4$ and the solvent was evaporated to obtain dry solid. The ester was isolated in quantitative yields. It was then recrystallized from diethyl ether and characterized by standard spectroscopic techniques.

The deprotection reactions were carried out on the ester and sensitizer solutions in PYREX tubes. The anionic sensitizers were generated in situ, whereas the neutral sensitizers were obtained from commercial sources. Since isolation of the released functionality is of utmost importance for most of the applications of this technique, phenylacetic acid was isolated and quantified for all the sensitizers. Approximately 20–50 mg each of the sensitizer and ester were dissolved in acetonitrile, purged with argon for about 10 minutes, and photolyzed with an appropriate filter using a xenon-arc lamp for about 2 h. The acid released was isolated using basic extraction (Banerjee, A. and Falvey, D. E., J. Org. Chem. 62:6245–6251 (1997)), weighed and characterized by spectroscopic techniques.

In order to determine the initial products, the solutions were examined by $^1$H NMR prior to work-up steps in certain cases. In these cases, nearly one equivalent sensitizer was added to a solution of the ester in $CD_3CN$. The tube was then sealed and purged with argon for about 10 minutes. The concentration of ester was determined by $^1$H NMR using an internal standard (hexamethyldisiloxane). The reaction mixture was then photolyzed using a xenon-arc lamp and an appropriate filter for about 2 h. The amount of acid released was determined by $^1$H NMR.

Scheme 7

The mechanism in Scheme 7 predicts that any sensitizer capable of delivering an electron to the phenacyl group will initiate the desired release of the carboxylate anion. The free energy change for this initial electron transfer is given by the difference between the excited state oxidation potential of the sensitizer ($E_{ox}$*) and $E_{red}$, the reduction potential of the phenacyl group (ca. −1.94 V vs. SCE). Maximal rates of electron transfer are usually seen when $\Delta G_{et}$ is at least 10 kcal/mol negative (Scannell et al., J. Am. Chem. Soc. 119:1971–1975 (1996)). Thus any sensitizer with $E_{ox}$*more negative than −19.V, more preferably, −2.0 V, ought to deliver an electron to the phenacyl substrate. This appears to be the case. All of the sensitizers that were effective have $E_{ox}$*values that ranged from −2.24 V to −3.25. Another criterion in choosing the sensitizer is its $E_{ox}$ values. If the $E_{ox}$ value of the sensitizer is sufficiently low so that it can transfer an electron to the ester from its ground states, then the undesirable dark reaction would occur. Thus all the successful sensitizers had $E_{ox}$ values ranging from 0.20 V to 1.1 V.

Figure 1A:
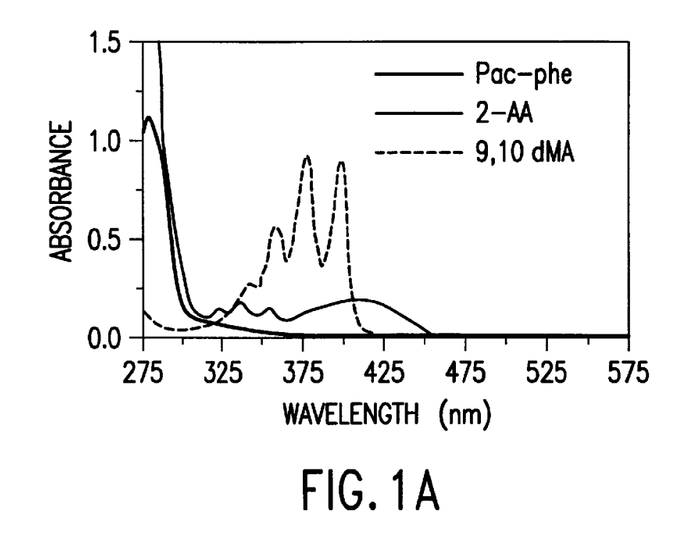
FIGS. 1A and 1B show graphs depicting the UV absorption of phenacyl phenylacetate (Pac-phe) and few of the sensitizers described herein. The phenacyl ester has a weak absorption tail above 300 nm. 9-Methylcarbazole (9-MC) has an absorption peak at 348 nm, whereas the anthracene derivatives have $\lambda_{max}$ close to 400 nm. 2-Aminoanthracene (2-AA) was the only sensitizer that absorbs above 400 nm. Therefore 2-aminoanthracene was used as the sensitizer for deprotection with visible light. (9,10 dMA=9,10-dimethylanthracene; 9-MA=9-methylanthracene.)
Figure 1B:
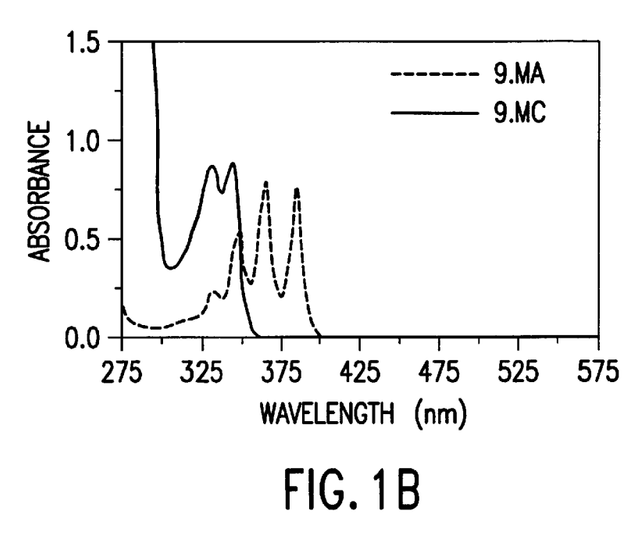

One important criteria for choosing the sensitizer was that it absorbs in or near the visible wavelengths. FIGS. 1A and 1B show the absorption spectra of some of the sensitizers and the phenacyl ester. The phenacyl ester has a weak absorption band above 300 nm corresponding to n-π*transition ($\epsilon_0^{320}$=60 $M^{-1}$ $cm^{-1}$), whereas the sensitizers (except 9-methylcarbazole) absorb near 400 nm. High wavelength cutoff filters (390 mn or 400 nm) were used in this study to ensure that the radiation was absorbed only by the sensitizers and not by the ester.

As seen in Table 2, sensitizers with absorption maxiina spanning from 332 nm to 407 nm are effective at promoting photorelease. Of the sensitizers examined in this study, 9,10-dimethylanthracene (No. 6) provided the highest yields and the shortest irradiation times while at the same time being excitable with high wavelength light. The monomethyl derivative, 9-methylanthracene (No. 4), is also an effective sensitizer. However its lower wavelength absorption band and its propensity for photodimerization render it somewhat less desirable than the dimethyl derivative. The highest wavelength sensitizer, 2-aminoanthracene (No. 7), allows for photolysis in the low wavelength visible region of the spectrum. However the required irradiation times are longer and the isolated yield is somewhat lower. Also examined were two anionic photosensitizers, 2-naphtholate and 2-phenanthrolate (Nos. 3 and 5) (Legros, B., et al., J. Phys. Chem. 95:4752–4761 (1991)). These are compatible with aqueous media (provided it is kept sufficiently basic). However in the absence of a sacrificial reductant (e.g. ascorbate), very low yields of product were obtained. Apparently the aryloxy radical formed in the initial electron transfer are unstable and consume the substrate and/or products through some uncharacterized side reactions. The conditions reported here use ascorbic acid. The latter regenerates the sensitizer by donating a H atom (or electron) to the aryloxy radical. N-Methylcarbazole (No. 2) also sensitizes release, although it absorbs at wavelengths only slightly higher than the original arylamines. Data from N,N,N,N-tetramethylphenylene diamine (Banerjee, A. and Falvey, D. E., J. Org. Chem. 62:6245–6251 (1997)) (No. 1) are included for comparison purposes.

The experiments here demonstrate that through the choice of an appropriate sensitizer, photolytic release of carboxylates can be achieved using light of wavelengths as high as 400 nm. In addition to the practical benefits of being able to control photolysis wavelengths, this also provides further confirmation of the proposed electron transfer mechanisn (Banerjee, A. and Falvey, D. E., J. Org. Chem. 62:6245–6251 (1997)).

TABLE 2

Photosensitized Release of Phenylacetic acid from Phenacyl Phenylacetate

| No. | Sensitizer | $\lambda_{max}$ (nm) | $E_{ox}$ (V vs. SCE) | $E_{ox}*$ (V vs. SCE) | Cond.[a] | % Yield (conv) |
|---|---|---|---|---|---|---|
| 1 | Me$_2$N—C$_6$H$_4$—NMe$_2$ | 332 | 0.20 | −3.25 | >320 nm, 2 h | 76 (100)[c] |
| 2 | N-methylcarbazole | 345 | 1.10 | −2.46 | >320 nm, 3 h | 88 (100)[c] |
| 3 | 2-naphtholate | 349 | 0.54 | −2.70 | 350 nm, 3 h[b] | 70 (100)[c] |
| 4 | 9-methylanthracene | 387 | 0.96 | −2.46 | >390 nm, 2 h<br>>320 nm, 2.5 h | 83 (29)[d]<br>78 (100)[c] |
| 5 | phenanthrolate | 382 | 0.34 | −2.57 | 350 nm, 3.5 h[b] | 86 (100)[c] |
| 6 | 9,10-dimethylanthracene | 398 | 0.87 | −2.23 | >390 nm, 2.0 h<br>>390 nm, 2.0 h | 90 (100)[c]<br>96 (100)[d] |
| 7 | 2-aminoanthracene | 407 | 0.44 | −2.25 | >400 nm, 15 h<br>>390 nm, 5 h | 97 (74)[d]<br>70 (90)[c] |

[a]Unless otherwise noted the irradiation were carried out on samples containing 20–50 mg each of the ester and sensitizer dissolved in 50 mL CH$_3$CN. Samples were purged with N$_2$ and then irradiated with a 350 W Xe lamp using high-pass glass filters.
[b]Irradiation carried out on solutions in Pyrex vessels using a Rayonette photoreactor with broad-band fluorescent lamps having emission maxima at 350 nm. The solutions consisted of 110 mg of ester, 130–180 mg sensitizer, 780–900 mg of ascorbic acid, and 1.1 g KOH, in 80% aqueous CH$_3$OH.
[c]Yields were determined gravimetrically following isolation of phenylacetic acid.
[d]Yields determined by $^1$H NMR integration of the phenylacetic acid peak relative to an internal standard. In these cases samples contained 10–20 mg each of ester and sensitizer, and 1–2 mL of CD$_3$CN.

These results show that is possible to extend the phenacyl/electrontransfer procedure to the photorelease of hydroxyl groups, phosphates and difunctional acids. In the case of the alcohols, it is not possible to deprotect simple phenacyl ethers via the electron transfer route. However the use of mixed phenacyl alkyl carbonates does allow for efficient deprotection. Analysis of the photoproducts from 9,10-dMA sensitized reactions shows that this sensitizer, like the alkylaryl amines, initiates the bond scission reactions via an initial electron transfer reaction. The cation radical of 9,10-dMA decays through deprotonation and subsequent radical coupling processes.

Having now generally described this invention, the same will be understood by reference to the following examples which are provided herein for purposes of illustration only and are not intended to be limiting unless otherwise specified.

EXAMPLES

General

Unless otherwise noted, materials were obtained from commercial suppliers and used without further purification. Acetonitrile and dichloromethane were distilled from $CaH_2$ under anhydrous $N_2$ atmosphere through a vacuum sealed column (30 cm) packed with glass helices. $^1H$ NMR spectra were run at 200 MHz and $^{13}C$ NMR spectra at 55.1 MHz on a Bruker AF200 spectrometer unless otherwise indicated. Preparative photolysis reactions were performed using either a 400 W Xe lamp or a Ace-Hanovia 450 W medium pressure Hg vapor lamp. The CW Xe arc lamp was also used to carry out control reactions. 295 nm (corex), 320 nm (Pyrex), 390 nm or 400 nm high pass cutoff filters were used to ensure that the light was absorbed by the sensitizer rather than the substrate. Gas chromatography-mass spectra (GC-MS) were obtained using a XTI®-5 (30 m bonded 5% phenyl) GC column with 0.25 mm internal diameter and 0.25 μm film thickness. Ar was used as the mobile phase. The temperature was increased from 50° C. to 300° C. in 20 minutes. The mass spectrum of each peak was obtained by EI.

Example 1

Phenacyl Alcohol (α-hydroxyacetophenone) 6

This procedure was adapted from the one developed by Pirkle and Simmons (Pirkle, W. H. and Simmons, K A., *J. Org. Chem.* 48:2520–2527 (1983)). 11.62 g (0.1706 moles) sodium formate was stirred in 50 ml ethanol for about 15 minutes. 5.31 g (26.7 mmol) phenacyl bromide was added to it and the mixture was refluxed under nitrogen at 105° C. for nearly 20 h. The reaction mixture was cooled and complete conversion of the starting material was confirmed by TLC. The solvent was evaporated and about 50 ml of boiling water was added and the solution was filtered hot. The filtrate was then cooled to precipitate out the alcohol. Yield 3.11 g (86%) from 5.31 g phenacyl bromide, white crystalline solid: mp 82–84° C. (lit. mp 84–85° C. (Pirkle, W. H. and Simmons, K A., *J. Org. Chem.* 48:2520–2527 (1983)); $^1H$ NMR ($CDCl_3$) δ6 3.49 (t, J=4.5), 4.87 (d, J=4.5), 7.44–7.65 (m, 3H), 7.91 (dd, $J_1$=8, $J_2$1.3, 2H); $^{13}C$ NMR ($CDCl_3$) δ198.4, 134.3, 133.5, 129.0, 127.7, 65.5; EI-MS, m/z (rel. intensity) 136 ($M^+$, 6), 105 (100), 77 (81), 52 (29).

Example 2

Phenacyl Diethylphosphate

The synthetic procedure was adapted from the one used by Givens et al. (Givens et al., *J. Am. Chem Soc.* 114:8708–8710 (1992); Givens et al., *J. Am. Chem. Soc.* 115:6001–6012 (1993)) for the synthesis of desylphosphates. To a solution of 1.38 g (10.1 mmol) phenacyl alcohol in 5 ml pyridine, 3 ml (20.8 mmol) diethyl phosphoryl chloride was added dropwise at −5° C. with constant stirring. The mixture was allowed to warm up to room temperature and stirred overnight under nitrogen. About 10 ml diethyl ether and 50 ml water was added to the mixture. The aqueous layer was extracted with diethyl ether. The organic layer was washed with 3×50 ml 1N $H_2SO_4$ followed by 3×50 ml 5M $NaHCO_3$ and about 50 ml water. The ether layer was treated with activated carbon, dried over anhydrous $MgSO_4$ and the ether was then evaporated. Yield 0.767 g (28%) from 1.38 g phenacyl alcohol, yellow oil; $^1H$ NMR ($CDCl_3$) δ1.30 (t, J=7, 6H), 4.15 (p, J=7,4H), 5.25 (d, J=10,2H), 7.38–7.58 (m, 3H), 7.83 (d, J=7,2H) $^{13}C$ NMR ($CDCl_3$) δ192.3, 192.2, 134.0, 133.9, 128.9, 127.7, 68.7, 68.6, 64.4, 66.3, 16.1, 16.0; EI-MS, m/z (rel. intensity) 272 ($M^+$, 2), 227 (12), 199 (13), 118 (67), 105 (100), 77 (80), 52 (47).

Example 3

Phenacyl Phenoxide (α-phenoxyacetophenone) 1c

Phenol (2.045 g, 21.8 mM) and 2.696 g (19.5 mM) potassium carbonate were dissolved in 40 ml acetone and the mixture was stirred for about 10 minutes. 3.532 g (17.7 mM) of phenacyl bromide was added to the mixture and the mixture was refluxed for 2 h. The reaction mixture was then quenched with 100 ml water and the phenacyl ether was extracted with (3×50 ml) diethyl ether. The organic extracts were washed with 2 M NaOH (3×50 ml), and water (3×50 ml), and dried over $MgSO_4$. The solvent was evaporated under reduced pressure and a white solid was obtained. The crude product was crystallized with ethanol. Yield 2.659 g (71%) from 3.53 g phenacyl bromide, white crystalline solid: mp 70–72° C. (lit. mp 71–72° C. (Netto-Ferreira et al., *J. Org. Chem.* 55:89–92 (1990)); $^1H$ NMR ($CDCl_3$) δ5.26 (s, 2H), 6.92–7.01 (m, 3H), 7.28 (t, J=7,2H), 7.45–7.65 (m, 3H), 7.99 (d, J=7,2H); $^{13}C$ NMR ($CDCl_3$) δ194.5, 158.0, 134.7, 133.8, 129.5, 128.8. 128.1, 121.6, 114.8, 70.8; EI-MS, m/z (rel. intensity) 213 (M+1, 5), 212 ($M^+$, 29), 106 (16), 105 (100), 91 (13), 77 (90), 65 (15), 50 (45).

Example 4

Phenacylisopropyl Carbonate

Methyltriflate (1 mL, 8.84 mmol) was added dropwise to a solution of (0.959 g, 5.92 mmol) carbonyl diimidazole dissolved in 20 ml nitromethane. The solution was kept at about 0° C. during the addition. The solution was then warmed to room temperature and was allowed to stir for 1 h. The solution was then transferred to a flask containing freshly azeotroped (from benzene) 0.647 g (5.303 mmol) phenacyl alcohol. The resulting mixture was allowed to stir for 2 h at room temperature to form the phenacyl carbonyl-N-methylimidazole (not isolated or characterized). Freshly azotroped isopropyl alcohol (5.92 mmol) was then added and the reaction mixture was stirred overnight. The solvent was removed by vacuum distillation and the product was purified using silica gel flash chromatography with 80% hexane and 20% ethyl acetate. Yield 1.032 g (88%) from 0.715 g phenacyl alcohol, yellow oil; $^1H$ NMR ($CDCl_3$, 400 MHz) δ3.87 (s, 3H), 5.37 (s, 2H), 7.46–7.62 (m, 3H), 7.92 (d, J=6, 2H); $^{13}C$ NMR ($CDCl_3$, 110 MHz) δ191.9, 154.2, 133.8, 128.7, 127.5, 72.6, 68.2, 21.5; EI-MS, m/z (rel. intensity) 222 ($M^+$, 1), 163 (27), 118 (32), 105 (100), 91 (60), 77 (66), 65 (13), 50 (44).

Example 5

Phenacyl 5'-thymidine Carbonate

Same procedure as for phenacyl-isopropylcarbonate except 100% ethylacetate was used in the chromatography. Yield 3.7 g (48%) from 4.6 g thymidine, white solid: mp 179–182° C.; $^1H$ NMR ($CDCl_3$, 400 MHz) δ1.76 (s, 3H), 2.08–2.23 (m, 2H), 3.95–3.97 (m, 1H), 4.27–4.57(m, 3H), 5.49 (d, J=4, 1H), 5.57 (s, 2H), 6.21 (t, J=7, 1H), 7.48 (s, 1H), 7.56 (t, J=7, 2H), 7.70 (t, J=7, 1H), 7.95 (d, J=7, 2H), 11.33 (s, 1H); $^{13}C$ NMR ($CDCl_3$, 110 MHz, δ192.6, 163.7, 154.3, 150.5, 135.8, 134.2, 133.6, 129.09 127.8, 109.9, 83.8, 83.5, 70.1, 69.3, 67.8, 38.6, 12.1: FAB-MS, m/z (rel.

intensity) 405 (M+1,8), 197(12), 195(14), 155(24), 152(26), 137(14), 135(37), 119(100), 105(16), 103(55), 101(21), 89(28), 87(27), 85(95), 81(45), 79(20), 77(20), 74(23), 56(42), 54(38); HRMS calcd for $C_{19}H_{21}N_2O_8$:404.12979, found: 405.12773.

Example 6

Phenacyl t-butyl Carbonate

Potassium tert-butoxide (0.543 g, 4.83 mM) and t-butyl alcohol (0.525 g, 7.08 mM) were stirred in 15 mL dry THF. The mixture was added to a suspension of carbonyldiimidazole (1.5 g, 9.26 mM) in 15 mL dry THF. The mixture was stirred at room temperature for about 14 h. Phenacyl alcohol (0.643 g, 4.73 mM) was added to the reaction mixture and stirred at 0° C. for 2 h. About 30 mL water was added to the mixture and the carbonate was extracted with (3×50 mL) dichloromethane. The carbonate was purified using 4:1 hexane ethyl acetate. Yield 0.429 g (38%) from 0.643 g phenacyl alcohol, yellow oil; 1H NMR (CDCl$_3$, 400 MHz) δ1.50 (s, 9H), 5.23 (s, 2H), 7.43–7.59 (m, 3H), 7.88 (d, J=7 Hz, 2); $^{13}$C NMR (CDCl$_3$, 400 MHz) δ192.3, 153.1, 134.1, 133.9, 128.8, 127.7, 83.0, 67.9, 27.7; FAB-MS, m/z (rel. intensity) 237 (M+1, 13),181 (100), 163 (14), 119 (21), 105 (49), 91 (21), 77 (9), 57 (73); HRMS calcd for (M+1) $C_{13}H_{17}O_4$; 237.1127, found: 237.1135.

Example 7

Phenacyl (2-phenethyl) Carbonate

Same procedure as for phenacyl t-butylcarbonate. Yield 1.11 g (74%) from 0.65 g phenethyl alcohol, yellow oil; $^1$H NMR (CDCl$_3$, 400 MHz) δ3.02 (t, J=7, 2H), 4.40 (t, j=7, 2H), 5.33 (s, 2H), 7.21–7.32 (m, 5H), 7.46–7.63 (m, 3H), 7.89 (d, J=7, 2H); $^{13}$C NMR (CDCl$_3$, 110 MHz) δ191.7, 154.8, 137.1, 134.0, 129.0, 128.9, 128.6, 127.8, 126.7, 69.0, 68.6, 35.1; FAB-MS, m/z (rel. intensity) 286 (M+2, 3), 284 (M+1, 16), 154 (15), 137 (16), 105 (100), 91 (24), 77 (20); HRMS calcd. for $C_{17}H_{17}O_4$:285.11267, found: 285.11326.

Example 8

Phenacylmethyl Carbonate

To a solution of 0.86 g (6.30 mmol) phenacyl alcohol in 25 ml pyridine, 1.22 g (12.9 mmol) of methyl chloroformate was added dropwise with constant stirring. The mixture was then heated at about 80° C. for 1 h. The reaction mixture was cooled and about 50 ml of diethyl ether was added to it. The mixture was then washed with 3×50 ml of 1 N H$_2$SO$_4$ followed by 3×50 ml satd. NaHCO$_3$ and 2×50 ml water. The organic layer was dried over anhydrous MgSO$_4$ and the solvent evaporated. The resulting yellow oil was purified by flash chromatography on silica gel using 1:4 mixture of ethyl acetate and hexane. Yield 0.096 g (8%) from 0.857 g phenacyl alcohol, yellow oil; $^1$HNMR (CDCl$_3$) δ3.87 (s, 3H), 5.37 (s, 2H), 7.46–7.62 (m, 3H), 7.92 (d, J=6, 2H); $^{13}$C NMR (CDCl$_3$) δ191.7, 155.5, 134.0, 128.9, 127.7, 68.7, 55.3; EI-MS, m/z (rel. intensity) 194 (M$^+$, 1), 118 (3), 105 (100), 91 (6), 77 (29), 50 (8).

Example 9

Phenacylethyl Carbonate

Procedure same as for methyl carbonate. (5 mL, 52 mM) ethylchloroformate in 10 mL pyridine and 0.7251 g, 5.33 mM phenacyl alcohol. Yield 0.664 g (60%) from 0.7251 g phenacyl alcohol (mp 41–43° C.).

Example 10

Phenacylbenzyl Carbonate

Benzyl choroformate (3 mL, 21 mM) was added dropwise to a solution of phenacyl alcohol (0.204 g, 1.5 mM) in 10 mL pyridine at 0° C. Solution stirred for about 16 h at room temperature. The mixture was dissolved in dichloromethane and was washed with 10% HCl (3×100 mL), satd NaHCO$_3$ (3×100 mL) and water (2×100 mL). The resulting solution was purified by chromatography (4:1 hexane and ethyl acetate) and recrystallized with diethyl ether. Yield 0.355 g (88%) from 0.204 g phenacyl alcohol, white solid: mp 49–51° C.; $^1$HNMR (CDCl$_3$, 400 MHz) δ5.23 (s, 2H), 5.35 (s, 2H), 7.32–7.62 (m, 8H), 7.89 (d, J=7 Hz, 2H); $^{13}$C NMR (CDCl$_3$, 400 MHz) δ191.7, 154.9, 134.9, 134.0, 133.9, 128.9, 128.6, 128.3,127.7,70.2,68.7; FAB-MS, m/z (rel. intensity) 271.1 (M+1, 11), 181 (12),120 (5),105 (28),91 (100),77 (12); HRMS calcd for (M+1) $C_{16}H_{15}O_4$:271.0971, found: 271.0972.

Example 11

Diphenacyl Malonate (7)

The procedure for ester synthesis has been published (Banerjee, A. and Falvey, D. E.,*J. Org Chem.* 62:6245–6251 (1997)). Yield 3.137 g (46%) from 8.057 g phenacyl bromide, white solid: mp 84–86° C.; $^1$H NMR(CDCl$_3$) δ3.77 (s, 2H), 5.43 (s, 4H), 7.46–7.70 (m, 6H), 7.91 (d, J=7, 4H), $^{13}$C NMR (CDCl$_3$) δ191.3, 165.6, 134.0, 128.9, 127.8, 66.9, 40.8; EI-MS, m/z (rel. intensity) 340 (M+, 0.03), 203 (2), 118 (12), 105 (100), 77 (23), 50 (5).

Example 12

Diphenacyl N-t-Boc-gluntamate (8)

Yield 0.166 g (82%)from 0.168 g, phenacylbromide, white solid: mp 110–112° C.; $^1$H NMR (CDCl$_3$) δ1.45 (s, 9H), 2.20–2.55 (m, 2H), 2.77 (t, J=7, 2H), 4.50–4–65 (m, 1H), 5.26–5.58 (m, 5H), 7.45–7.66 (m, 6H), 7.88–7.94 (m 4H); $^{13}$C NMR(CDCl$_3$) δ192.1, 191.4, 172.3, 171.7, 155.4, 134.2, 134.0, 133.9, 128.9, 127.8, 80.0, 66.6, 66.1, 52.9, 29.9, 28.3, 27.7; FAB-MS, m/z (rel. intensity) 484 (M+1, 3), 385 (15), 384 (63), 248 (17), 220 (21), 137 (25), 119 (15), 105 (28), 91 (21), 84 (96), 77 (15), 73 (13), 57 (100), 56 (23), 55 (28); HRMS calcd for $C_{26}H_{30}NO_8$: 484.19714, found: 484.19695.

Example 13

Photorelease and Analysis of Alcohols

About 10–20 mg (~5×10$^{-5}$ moles) of the phenacyl ester or the carbonate, and 1.5 equivalents of the sensitizer were dissolved in 1 ml deuterated acetonitrile along with 0.5 equiv. of hexamethyldisiloxane as an internal standard. The solution was then transferred to a sealed NMR tube and purged with N$_2$ for about 15 minutes. The IH NMR spectrum of the mixture was taken and the CH$_2$ peak areas were determined and compared with that of the standard. The solution was then photolyzed with a 350 W Xe-arc lamp with a 395 nm glass cutoff filter (320 cutoff for 9-methylcarbazole) for 2 hours. The $^1$H NMR spectrum was taken again and the relevant peak areas of the products, unconverted starting materials and the standard were compared and the yields determined.

Example 14

Photolysis of Phenacyl 5'-Thymidine Carbonate and Isolation of the Released Alcohol

About 100 mg (2.5×10$^{-4}$ mol) of phenacyl 5'-thymidine carbonate and about 5×10$^{-4}$ moles (2 equivalents) of the sensitizer were dissolved in freshly distilled CH₃CN, purged with N₂ for 10 minutes and then photolyzed for nearly 3 h using a medium pressure Xe-arc lamp with a 395 nm cutoff filter (320 nm for 9-methylcarbazole and TMPD). The solvent was then removed under reduced pressure and the residue was washed several times with CH₂Cl₂. The insoluble white solid was dried, weighed and confirmed as thymidine by ¹H NMR.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. A compound having the Formula:

wherein

R¹ is an aryl or heteroaryl group; and

X is one of OCO₂R² or OP(O)(OR³)₂, wherein R² and R³, each independently, are the residue of an alcohol containing compound.

2. The compound of claim 1, wherein R² and R³ are independently alkyl, alkenyl, alkynyl, aryl, aralkyl, aralkenyl, aralkynyl, fused aryl, carbocyclic, carbocyloalkyl-substituted alkyl, heterocycloalkyl, heterocycloalkyl-substituted alkyl, heteroaryl, heteroarylalkyl, heteroarylalkenyl, or heteroaralkynyl, any one of which may be optionally substituted with one or more alkyl, alkenyl, alkynyl, alkoxy, acyl (alkanoyl), acyloxy, cyano, alkylcarboxy, chloro, bromo, aryl, cycloalkyl, aralkyl, aralkenyl, aralkynyl, hydroxy, nitro, amino or carboxy groups.

3. The compound of claim 1, wherein R² and R³ are the residue of a sugar or sugar derivative.

4. The compound of claim 1, which is phenacyl 5-thymidine carbonate.

5. The compound of claim 1, which has the Formula:

6. The compound of claim 1, which has the Formula:

* * * * *